US007863272B2

(12) United States Patent
Oksenberg et al.

(10) Patent No.: US 7,863,272 B2
(45) Date of Patent: Jan. 4, 2011

(54) SIGMA LIGANDS FOR NEURONAL REGENERATION AND FUNCTIONAL RECOVERY

(75) Inventors: Donna Oksenberg, Palo Alto, CA (US); Roman Urfer, Belmont, CA (US)

(73) Assignee: M's Science Corporation, Minatojima-minamimachi, Chou-ku, Kobe (JP)

( * ) Notice: Subject to any disclaimer, the term of this patent is extended or adjusted under 35 U.S.C. 154(b) by 1332 days.

(21) Appl. No.: 10/868,423

(22) Filed: Jun. 14, 2004

(65) Prior Publication Data

US 2005/0059689 A1    Mar. 17, 2005

Related U.S. Application Data

(60) Provisional application No. 60/478,735, filed on Jun. 12, 2003, provisional application No. 60/478,329, filed on Jun. 12, 2003, provisional application No. 60/498,132, filed on Aug. 26, 2003, provisional application No. 60/552,613, filed on Mar. 12, 2004.

(51) Int. Cl.
*A61K 31/50* (2006.01)
*A01N 43/60* (2006.01)

(52) U.S. Cl. .................. 514/249; 514/247; 514/248; 514/282

(58) Field of Classification Search ........................ None
See application file for complete search history.

(56) References Cited

U.S. PATENT DOCUMENTS

| 5,055,470 | A | 10/1991 | Boissard et al. |
| 5,229,394 | A | 7/1993 | Salazar-Grueso |
| 5,665,725 | A | 9/1997 | Moltzen et al. |
| 5,736,546 | A | 4/1998 | Kawashima et al. |
| 6,087,346 | A | 7/2000 | Glennon et al. |
| 6,436,938 | B1 | 8/2002 | Howard, Jr. |
| 2003/0087840 | A1 | 5/2003 | Lai et al. |
| 2005/0032827 | A1 | 2/2005 | Oksenberg et al. |
| 2006/0014753 | A1 | 1/2006 | Shamloo et al. |
| 2006/0052386 | A1 | 3/2006 | Wieloch et al. |

FOREIGN PATENT DOCUMENTS

| WO | WO/91/03243 A | 3/1991 |
| WO | WO/93/09094 A | 3/1993 |
| WO | WO/94/24116 A | 1/1994 |
| WO | WO/96/05185 A | 2/1996 |
| WO | WO/99/24436 A | 5/1999 |
| WO | WO/01/74359 A | 10/2001 |

OTHER PUBLICATIONS

Kidwell et al. (Stroke 2001, 32: 1349-1359).*
Cheng et al. ("Neuroprotection for ischemic stroke," NeuroRx Jan. 2004, vol. 1, 36-45).*
Pollack & Disler ("Rehabilitation of patients after stroke," The Medical Journal of Australia 2002, 177(8): 452-456).*
Long et al., "Selective Sigma Ligands Protect Against Dynorphin A-Induced Spinal Cord Injury in Rats," *Society for Neuroscience Abstracts*, vol. 16, 1990, No. 461.4.
Fujimura et al., "Synthesis, Structure and Quantitative Structure-Activity Relationships of σ Receptor Ligands, 1-[2-(3,4-Dimethyxyphenyl)ethyl]-4-(3-phenylpropyl) piperazines," *Bioorganic and Medicinal Chemistry*, vol. 5, No. 8, 1997, pp. 1675-1683.
Lobner, Doug and Lipton, Peter, "σ-Ligands and non-competitive NMDA antagonists inhibit glutamate release during cerebral ischemia", Neuroscience Letters, 1990, pp. 169-174, Elsevier Scientific Publishers, Ireland.
Manallack, David T. and Beart Philip M., "Quantitative conformational analyses predict distinct receptor sites for PCP-like and σ drugs", European Journal of Pharmacology, 1987, pp. 231-235, Elsevier.
Perregaard, Jens, "σ-Ligands with Subnanomolar Affinity and Preference for the $\sigma_2$ Binding Site. 1. 3-(ω-Aminoalkyl)-1H-indoles", Journal of Medicinal Chemistry, 1995, pp. 1998-2008, vol. 38, No. 11.
Pontecorvo, Michael J., "Possible Cerebroprotective and In Vivo NMDA Antagonist Activities of Sigma Agents", Brain Research Bulletin, 1991, pp. 461-465, vol. 26, Pergamon Press, United States.
Senda, Toshihiko, "Effect of SA4503, a novel $\sigma_1$ receptor agonist, against glutamate neurotoxicity in cultured rat retinal neurons", European Journal of Pharmacology, 1998, pp. 105-111, Elsevier.
Miyaoka et al., "Fluvoxamine for the Treatment of Depression and Parkinsonism in Progressive Supranuclear Palsy", International Journal of Psychiatry in Clinical Practice, 2002, pp. 45-47, vol. 6, No. 1.
Tottori, et al., "Attenuation of Scopolamine-Induced and Age-Associated Memory Impairments by the Sigma and\ 5-hydroxytryptamine1A receptor agonist OPC-14523", Journal of Pharmacology and Experimental Therapeutics, 2002, pp. 249-257, vol. 301, No. 1.
Tucker et al., "Fluvoxamine Reduces Physiologic Reactivity to Trauma Scripts in Posttraumatic Stress Disorder", Journal of Clinical Psychopharmacology, 2000, pp. 367-372, vol. 20, No. 3.
Shuaib et al., NEJM, 357(6): 562-571 (Aug. 2007).
Endres et al., Cerebrovasc. Dis., 25: 268-78 (2008).

(Continued)

*Primary Examiner*—Ardin Marschel
*Assistant Examiner*—Amy A Lewis
(74) *Attorney, Agent, or Firm*—Paul N. King, Esq.

(57) ABSTRACT

The invention discloses methods and compositions useful for facilitating neuronal regeneration and functional recovery in neurodegenerative diseases. The methods and compositions utilize ligands for the sigma receptor, wherein the ligand is preferably SA-4503, or salts, or solvates thereof. These molecules can be delivered alone or in combination with agents which treat or prevent neurodegenerative diseases such as those caused by ischemic stroke, diabetic peripheral neuropathy, cancer therapy induced neuropathy, multiple sclerosis, amyotrophic lateral sclerosis, traumatic brain injury, spinal cord injury, Huntington's disease or Parkinson's disease. In other methods, the sigma receptor ligands are administered after stroke to facilitate functional recovery. The administration of the sigma receptor ligands effects faster functional recovery.

22 Claims, No Drawings

OTHER PUBLICATIONS

Arvidsson et al., Nat. Med., 8(9): 963-70 (Sep. 2002).
Johansson et al., J. Cereb. Blood Flow & Metab., 22: 89-96 (2002).
Metz et al., Behavioural Brain Research, 162:71-82 (2005).
Dancause et al., J. Neuroscience, 25(44): 10167-79 (Nov. 2005).
Zhang et al., Stroke, 36: 847-52 (2005).
Lee et al., J. Neuroscience, 24(27): 6209-17 (Jul. 2004).
Chen et al., PNAS USA, 99: 9031-36 (2002).
Wieloch et al, Curr. Opin. Neurobiology, 6: 1-7 (2006, article in press).
Martin et al., Trends Neuroscience, 17: 251-57 (1994).
Dingledine et al., Pharmacol. Rev., 51(1): 7-61 (1999).
Zlokovic, Nat. Med., 12: 390-1 (2006).
Maurice, T., Drug News and Perspectives, 15(10): 617-25 (2002).
Maurice et al., Brit. J. Pharmacol., 127(2): 335-42 (May 1999).
Takahashi et al., Stroke, 26(9): 1676-82 (1995).
Earley et al., Neurochem. Internatl., 28(5-6): 509-21 (1996).
Matsuno et al., CNS Drug Rev., 4(1): 1-24 (1998).
Heading, C., Curr. Opin. Invest. Drugs, 2(2): 266-70 (2001).
Nakazawa et al., Neurochem. Internatl., 32: 337-43 (1998).
Chen, et al., Ann.Neurol., 53: 743-51 (2003).
Hoffman, et al., Program# 381.1/AA12, 2007 Neuroscience Meeting Planner, Society for Neuroscience (2007).

\* cited by examiner

SIGMA LIGANDS FOR NEURONAL REGENERATION AND FUNCTIONAL RECOVERY

CROSS-REFERENCE TO RELATED APPLICATIONS

This application claims the benefit of U.S. provisional patent application Nos. 60/478,735 filed on Jun. 12, 2003, 60/478,329 filed on Jun. 12, 2003, 60/498,132 filed on Aug. 26, 2003 and 60/552,613 filed on Mar. 12, 2004, all of which are herein incorporated by reference in their entirety.

FIELD OF THE INVENTION

The present invention relates to methods of treatment to achieve neuronal regeneration in subjects with neurodegenerative disorders. In particular, the present invention relates to the use of sigma receptor ligands to facilitate neuronal regeneration and functional recovery in subjects after neurodegenerative disease.

BACKGROUND OF THE INVENTION

The existence of the sigma receptor was proposed by Martin et al. (1976) J. Pharmacol. Exp. Ther. 197: 517-532 to explain the psychotomimetic effects of benzomorphans. Initially, the sigma receptor was thought to be a novel opioid receptor. However, the binding of the benzomorphans to the sigma receptor is not antagonized by naloxone, the classic opioid receptor antagonist. Further, the benzomorphans bind to a site that is distinct from the phencyclidine receptor on the N-methyl-D-aspartate (NMDA) receptor complex. Thus, the sigma receptor is established as a unique receptor.

The sigma receptor consists of two subtypes, named sigma-1 and sigma-2. Hellewell and Bowen (1990) Brain Res., 527: 224-253 were the first to define the characteristics of the two putative sigma receptor subtypes. The primary pharmacological distinction between these two sites is the affinity of the (+) isomers of the benzomorphan opiates for the binding sites. These compounds, such as (+)SKF 10,047 (NANM) and (+)pentazocine show nearly two orders of magnitude higher affinity for the sigma-1 site compared to the sigma-2 site. The (−) isomers of the benzomorphans show little selectivity between these two sites. Other distinctions noted between the two sites are a preponderance of the sigma-2 sites in cell lines such as NCB-20, PC12 and NG108-15 cells (Hellewell and Bowen; Quirion, R., et al., (1992) Trends in Pharmacological Sciences, 13: 85-86). The sigma-1 receptor has been identified and cloned, but not the sigma-2 receptor (Langa et. al., European Journal of Neuroscience, Vol. 18., 2003, pages 2188-2196). The endogenous ligands for sigma receptors are unknown.

The subcellular distribution of sigma-1 receptors in brain includes the hippocampus, cortex layer and olfactory bulb. Sigma-1 is a 26 kDa protein, and the gene encoding the receptor has been cloned. Hydropathy analysis suggested that the sigma-1 receptor has two transmembrane segments. Further, the sigma-1 receptors share no homology with any other known mammalian proteins.

Both types of the sigma receptors are expressed in the central nervous system as well as in peripheral tissues. Therefore, ligands for the receptor could be used for the treatment and prevention of neurodegenerative diseases. Consequently, brain sigma receptors have been the subject of intense investigation (Sonders et al. (1988) Trends Neurosci., 1: 37-40). In general, sigma receptors exhibit promiscuous binding to a wide variety of ligands such as psychotic drugs, antidepressants and neurosteroids. They have been demonstrated to play important roles in learning and memory in animal models of amnesia as well as in behavioral models of depression. Numerous studies have demonstrated robust neuroprotective properties of sigma receptor ligands in animal models of cerebral ischemia. The mechanism of neuroprotection for some of these sigma ligands has been controversial because both the sigma receptors and the phencyclidine (PCP) binding sites of the NMDA receptor channel complex have been reported to contribute to these effects.

Neurodegenerative diseases are characterized by the dysfunction and death of neurons, leading to the loss of functions mediated by the brain, spinal cord and the peripheral nervous system. These disorders have a major impact on society. For example, approximately 4 to 5 million Americans are afflicted with the chronic neurodegenerative disease known as Alzheimer's disease. Other examples of chronic neurodegenerative diseases include diabetic peripheral neuropathy, multiple sclerosis, amyotrophic lateral sclerosis, traumatic brain injury, spinal cord injury, Huntington's disease and Parkinson's disease. Normal brain aging is also associated with loss of normal neuronal function and may entail the depletion of certain neurons.

Stroke is the third ranking cause of death in the United States, and accounts for half of neurology inpatients. Depending on the area of the brain that is damaged, a stroke can cause coma, paralysis, speech problems and dementia. The major causes of cerebral infarction are vascular thrombosis, cerebral embolism, hypotension, hypertensive hemorrhage, and anoxia/hypoxia. However, the adult brain retains capacity for plasticity and functional reorganization throughout the life span, even after stroke or brain ischemia. Neuronal connections are continuously remodeled. The potential capability of the brain to compensate for the damaged part of the brain has relevance for stroke rehabilitation. Neuroimaging in stroke patients suggests some functional reorganization. Thus, one aspect of brain plasticity is that in stroke patients, the neuronal connections can be modified by sensory input, experience and learning, and the brain can respond by functional and structural reorganization, upregulation or downregulation of a neural response to an event, and the establishment of new functional and structural connections by collateral sprouting and compensatory synaptogenesis, as well as neurogenesis.

However, aside from the effect of the environmental factors on brain plasticity, drugs and the interactions between drugs and environmental factors are another aspect to be considered. Thus, the need continues to exist for new drugs and new methods for the treatment of central nervous system disorders and other conditions that take advantage of brain plasticity to assist neuronal regeneration and functional recovery. The present invention fulfills these and other needs.

Several sigma receptor ligands have been found to be neuroprotective (i.e. to protect against neuronal cell death and consequential loss of function) in predictive models used for the testing of drugs for neuroprotective activity. For example, the sigma receptor ligand opipramol was found to protect against ischemia in gerbils and was found to modulate the NMDA-type of glutamate receptors. In addition, other sigma ligands, including BMY-14802, caramiphen and haloperidol, exhibited properties in in vivo models that were consistent with affording protective effects against NMDA-induced toxicity and seizures (M. Pontecorvo et al., (1991) Brain Res. Bull., 26:461-465), and several sigma ligands were found to inhibit ischemia-induced glutamate release from hippocampal slice preparations in vitro (D. Lobner et al., (1990) Neuroscience Lett., 117:169-174).

U.S. Pat. No. 5,736,546 discloses certain 1,4-(diphenylalkyl) piperazine derivatives that are ligands for sigma receptors. One of the compounds, 1-(3,4-dimethoxyphenethyl)-4-(3-phenylpropyl) piperazine, is now also known as SA4503. Nakazawa et al., Neurochem. Int., 32 (1998), 337-343 report that SA4503 is a selective sigma-1 agonist and was found to significantly suppress hypoxia/hypoglycemia-induced neurotoxicity in rat primary neuronal cultures. This neuroprotective action led the authors to suggest that sigma-1 receptors may be useful in the treatment of neurodegeneration (see page 342). Senda et al., European Journal of Pharmacology, 342 (1998), 105-111 further report that SA4503 was found to be active against glutamate neurotoxicity in cultured rat retinal neurons. The authors suggest that sigma-1 receptor agonists may be useful against retinal diseases with neuronal cell death due to ischemia, such as central and branch retinal artery occlusion, diabetes mellitus, age-related macular degeneration, hemoglobinopathies and various types of glaucoma. SA4503 is currently undergoing clinical development for the treatment of depression, and has also been noted as having potential use in the treatment of dementia and drug dependence.

U.S. Pat. No. 5,665,725 discloses certain piperidine derivatives that are ligands for sigma receptors. The compounds are said to be useful in the treatment of anxiety, psychosis, epilepsy, convulsion, movement disorders, motor disturbances, amnesia, cerebrovascular diseases, senile dementia of the Alzheimer type and Parkinson's disease. One of the compounds, 1'-[4-[1-(4-fluorophenyl)-1H-indol-3-yl]-1-butyl] spiro [isobenzofuran-1(3H),4'-piperidine], is also known as Lu 28-179 or siramesine. It is a selective sigma-2 agonist and also displays activity towards the sigma 1 receptor (Perregaard J., et al., J. Med. Chem., 1995, 38, pages 1998-2008). International patent application, publication number WO 99/24436 further discloses that the hydrohalide salts of the compound, in particular the hydrochloride salt, have good bioavailability.

Thus the art suggests that sigma ligands may be useful as neuroprotective agents in the treatment of subjects with neurodegenerative diseases.

Unexpectedly, it has now been found that certain sigma ligands facilitate functional recovery in subjects suffering from neurodegenerative disease. Thus, the sigma ligands are useful as neuroregenerative agents in the treatment of neurodegenerative disease following a neuronal insult.

SUMMARY OF THE INVENTION

The present invention provides methods and compositions for treating neurodegenerative diseases. The sigma receptor ligands of the invention enhance functional recovery and neuronal regeneration. These molecules can be delivered alone or in combination with additional agents, and are used as neuronal regeneration agents for the treatment of neurodegenerative diseases such as those resulting from ischemic strokes or other insults that injure neurons.

Accordingly, in one aspect, the subject invention is directed to a method for treating or preventing neurodegenerative disease in a subject in need thereof. The method comprises administering to the subject a pharmaceutically effective amount of a ligand for the sigma receptor.

The invention thus provides methods for treating neurodegenerative disease in a mammalian subject in need thereof to facilitate neuronal regeneration leading to functional recovery after a neurodegenerative disease, the method comprising administering a pharmaceutically effective amount of a sigma receptor ligand to the subject.

In another aspect, the present invention provides the use of a sigma ligand in the manufacture of a medicament to facilitate neuronal regeneration leading to functional recovery in a mammalian subject after a neurodegenerative disease.

In yet another aspect, the present invention provides a pharmaceutical composition, which comprises a sigma ligand for treating a mammalian subject to facilitate neuronal regeneration leading to functional recovery after a neurodegenerative disease.

The neurodegenerative disease can be ischemic stroke, Alzheimer's disease, diabetic peripheral neuropathy, cancer therapy induced neuropathy, multiple sclerosis, amyotrophic lateral sclerosis, traumatic brain injury, spinal cord injury, Huntington's disease or Parkinson's disease, but is preferably ischemic stroke, traumatic brain injury, or spinal cord injury. Further, the invention provides methods for administering an additional active agent. The ligands of the invention may be administered in a pharmaceutical composition containing a pharmaceutically acceptable excipient. The excipient may be suitable for oral administration. Thus, the composition may be in the form of a tablet, a capsule, or a soft-gel capsule.

Alternatively, the excipient may be liquid suited to intravenous, intramuscular, or subcutaneous administration. Alternatively, the excipient may be suited to transdermal administration, or buccal administration. The sigma receptor ligand is preferably 1-(3,4-dimethoxyphenethyl)-4-(3-phenylpropyl) piperazine (SA 4503), or a pharmaceutically acceptable salt, or solvate thereof.

The present invention provides methods and compositions for the rehabilitation of patients with a central nervous system disorder, such as stroke, spinal cord ischemia, spinal cord injury and traumatic brain injury. The invention is based on the discovery that sigma receptor ligands, preferably SA-4503, when administered to patients, within about 48 hours after a stroke, and for a period of one to three months, preferably administered up to one year, or more preferably, administered continuously, allows the patients to recover from the dysfunctional state. The ligand can be delivered alone or in combination with additional agents. SA-4503 may be administered, for example, daily over the course of the treatment.

Accordingly, in one aspect, the subject invention is directed to a method for treating stroke in a subject, which comprises administering to the subject a pharmaceutically effective amount of a ligand for the sigma receptor immediately after a stroke episode and for a period of one to three months. The ligand for the sigma receptor is preferably 1-(3, 4-dimethoxyphenethyl)-4-(3-phenylpropyl) piperazine (SA 4503), or a pharmaceutically acceptable salt, or solvate thereof, such as the HCl salt or the dihydrochloride salt of SA SA-4503.

In another aspect of the invention, the administration of the sigma ligand to the subject commences not less than 24 hours, such as not less than 48 hours, one week, one month or three months, after a neurodegenerative disease, especially after an ischemic stroke, traumatic brain injury or spinal cord injury. From the start of the treatment, the sigma ligand can be administered repeatedly, for example daily, for a period of, for example, one week, two weeks, one month, three months, one year or longer. For example the treatment can start at least 24 hours, or at least 48 hours, at least one week after an ischemic stroke, traumatic brain injury or spinal cord injury, and continue for one month, three months, six months or one year.

The treatment of the subject can be conducted under the direction of a physician. In the course of the treatment, the physician may assess the subject for evidence of neuronal regeneration. The evidence can be evidence of functional recovery or of a structural change in the brain or spinal cord. Thus, for example, the physician can measure one or more functional responses of the subject immediately prior to, or on commencement of the treatment, and again after treatment. Thus, treatment can be continued until evidence of neuronal regeneration (or functional recovery) has been obtained.

As described in more detail hereinafter, the evidence of functional recovery may be, for example, recovery in a motor skill, cognitive skill, speech or sensory perception and function. Particular mention may be made of recovery in a motor skill and recovery in a cognitive skill. Evidence of neuronal regeneration may also be evidence of a structural change in the brain or spinal cord.

In another aspect of the invention, a packaged kit is provided for a patient to use in the treatment of a neurodegenerative disease to facilitate neuronal regeneration (or functional recovery). The kit includes a pharmaceutical formulation of SA-4503, or salts or solvates thereof, a container housing the pharmaceutical formulation during storage and prior to administration, and instructions, e.g., written instructions on a package insert or label, for carrying out drug administration in a manner effective to treat the neurodegenerative disease to facilitate neuronal regeneration (or functional recovery). The pharmaceutical formulation may be any formulation described herein, e.g., an oral dosage form containing a unit dosage of the ligand for the sigma receptor, the unit dosage being a therapeutically effective dosage for treatment of the disease.

These and other aspects of the present invention will become evident upon reference to the following detailed description. In addition, various references are set forth herein which describe in more detail certain procedures or compositions, and are therefore incorporated by reference in their entirety.

DETAILED DESCRIPTION

I. Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art.

The term "agonist" means a molecule such as a compound, a drug, an enzyme activator or a hormone that enhances the activity of another molecule or the activity of the sigma receptor site.

The term "antagonist" means a molecule such as a compound, a drug, an enzyme inhibitor, or a hormone, that diminishes or prevents the action of another molecule or the activity of the sigma receptor site.

The term "stroke" broadly refers to the development of neurological deficits associated with impaired blood flow to the brain regardless of cause. Potential causes include, but are not limited to, thrombosis, hemorrhage and embolism. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss.

By "ischemic episode" is meant any circumstance that results in a deficient supply of blood to a tissue. When the ischemia is associated with a stroke, it can be either global or focal ischemia, as defined below. The term "ischemic stroke" refers more specifically to a type of stroke that is of limited extent and caused due to blockage of blood flow. The term "ischemic stroke" includes cerebral ischemia after cardiac arrest, stroke, and multi-infarct dementia, including those resulting from surgery. Cerebral ischemic episodes result from a deficiency in the blood supply to the brain. The spinal cord, which is also a part of the central nervous system, is equally susceptible to ischemia resulting from diminished blood flow.

By "focal ischemia," as used herein in reference to the central nervous system, is meant the condition that results from the blockage of a single artery that supplies blood to the brain or spinal cord, resulting in damage to the cells in the territory supplied by that artery.

By "global ischemia," as used herein in reference to the central nervous system, is meant the condition that results from a general diminution of blood flow to the entire brain, forebrain, or spinal cord, which causes the death of neurons in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

By "neuroprotective agent" as used herein is meant a compound effective to reduce neuronal cell death, including the ability to inhibit the spread of neuronal damage from the initial site of injury.

The term "microarray" refers to an array of distinct polynucleotides or oligonucleotides synthesized or attached or deposited on a substrate, such as paper, nylon or other type of membrane, filter, chip, glass slide, beads, or any other suitable solid support, at a desired density.

The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an "effective amount" for therapeutic uses is the amount of the composition comprising a ligand for the sigma receptor disclosed herein required to provide a clinically significant decrease in neurodegenerative disease, such as those resulting from ischemic stroke. An appropriate "effective" amount in any individual case may be determined by one of ordinary skill in the art using routine experimentation.

As used herein, the terms "treat" or "treatment" are used interchangeably and are meant to indicate a postponement of development of neurodegenerative diseases and/or a reduction in the severity of such symptoms that will or are expected to develop. The terms further include ameliorating existing neurodegenerative symptoms, treating additional symptoms, and ameliorating the underlying metabolic causes of symptoms.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

By "physiological pH" or a "pH in the physiologically acceptable range" is meant a pH in the range of approximately 7.2 to 8.0 inclusive, more typically in the range of approximately 7.2 to 7.6 inclusive.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

The term "pharmaceutically acceptable salt" of a compound means a salt that is pharmaceutically acceptable and that possesses the desired pharmacological activity of the parent compound. Such salts, for example, include:
(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;
(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "optional" or "optionally" means that the subsequently described event or circumstance may or may not occur, and that the description includes instances where the event or circumstance occurs and instances where it does not. For example, the phrase "optionally another drug" means that the patient may or may not be given a drug other than the sigma receptor ligands. "Another drug" as used herein is meant any chemical material or compound suitable for administration to a mammalian, preferably human, which induces a desired local or systemic effect. In general, this includes: anorexics; anti-infectives such as antibiotics and antiviral agents, including many penicillins and cephalosporins; analgesics and analgesic combinations; antiarrhythmics; antiarthritics; antiasthmatic agents; anticholinergics; anticonvulsants; antidiabetic agents; antidiarrheals; antihelminthics; antihistamines; antiinflammatory agents; antimigraine preparations; antinauseants; antineoplastics; antiparkinsonism drugs; antipruritics; antipsychotics; antipyretics; antisense agents; antispasmodics; cardiovascular preparations including calcium channel blockers and beta-blockers such as pindolol; antihypertensives; central nervous system stimulants; cough and cold preparations, including decongestants; diuretics; gastrointestinal drugs, including $H_2$-receptor antagonists; sympathomimetics; hormones such as estradiol and other steroids, including corticosteroids; hypnotics; immunosuppressives; muscle relaxants; parasympatholytics; psychostimulants; sedatives; tranquilizers; thrombolytics; neuroprotectants; radical scavengers and vasodilators.

The term "functional rehabilitation" as used herein means physical therapy, occupational therapy, and the like. It is anticipated that drug treatment will commence with rehabilitation.

II. Sigma Receptor

The Sigma Receptor was identified from a microarray analysis of an enriched environment experiment. The invention further provides methods for the identification of compounds that modulate the expression of the sigma receptor for the treatment of central nervous system disorders and for stimulating nerve cell survival and regeneration in subjects with neurodegenerative disorders. The microarray analysis identified genes that are differentially expressed after cortical ischemia and postischemic environmental enrichment brain tissue, relative to their expression in normal, or non-enriched environment are identified and described Further, the invention provides methods of treating a subject exhibiting changes in the above gene expression, wherein the therapeutic intervention results in cell genesis and an enhanced subsequent functional recovery in brain. The inventors have found that sigma receptors expression decrease in the vulnerable regions after middle cerebral artery occlusion (MCAO) in standard conditions and increase after MCAO when the subject is exposed to conditions of enriched environment. An increase has also been detected after MCAO in the resistant regions of the brain. Thus, for a subject suffering from focal or global ischemia of the brain, sigma receptor ligands are administered after the insult, and for a period of time sufficient to facilitate functional recovery. The pharmaceutical intervention leads to faster functional recovery.

In one aspect, an array or a micro array can be used to obtain the gene expression of interest. Typically, probe oligonucleotides are immobilized on a solid support, and then contacted with a sample containing labeled target oligonucleotides under hybridization conditions to produce a hybridization pattern. After hybridization, the fluorescence or radioactivity, such as $^{33}P$ utilized for in situ hybridization, measurements are analyzed to determine the level of hybridization of the targets to the probes. The information is useful in determining gene function, gene-splicing, understanding the genetic basis of disease, diagnosing disease, in developing and monitoring the activity of therapeutic agents, detecting the presence or absence of a polymorphism, and the like (Heller, R. et al. (1997) Proc. Natl. Acad. Sci. 94:2150-55). The probe and target oligonucleotides can be obtained from the RNA or DNA of a biological sample. The oligonucleotides will generally be a DNA that has been reverse-transcribed from RNA derived usually from a naturally occurring source, where the RNA can be total RNA, PolyA+mRNA, amplified RNA and the like. The initial mRNA sample may be derived from a physiological source including a single-celled organism such as yeast, from a eukaryotic source, or a multicellular organism including plants and animals, particularly mammals and organs, tissues, and cells derived from the mammals such as from any bodily fluids (such as blood, urine, saliva, phlegm, gastric juices, etc.), cultured cells, biopsies, or other tissue preparations. Methods of isolating RNA from cells, tissues, organs or whole organisms are known to those of skill in the art and are described in Sambrook, Fritsch & Maniatis (1989) Molecular Cloning: A Laboratory Manual (Cold Spring Harbor Press). ). In particular, RNA from the brain, such as from medial, rostral, frontal, hippocampus and striatum regions of the subject are purified and cloned for use in the microarray experiments.

The hybridization pattern can be used to determine quantitative information about the genetic profile of the nucleic acids in the sample that was contacted with the array to generate the hybridization pattern, as well as the physiological source from which the labeled sample nucleic acid was derived. The data provides information about the physiological source from which the sample nucleic acids were derived, such as the types of genes expressed in the tissue or cell which is the physiological source, as well as the levels of expression of each gene, particularly in quantitative terms.

It was discovered that rats subjected to MCAO and then exposed to an enriched environment demonstrated upregulation of the type 1 sigma receptor mRNA in striatum and frontal cortex and a downregulation of the receptor in medial cortex. The frontal cortex has been implicated in control of sensory-motor function. Hence the role of pharmacological interventions in the postischemic rehabilitation phase. Thus, the administration of sigma receptor ligands, such as sigma receptor agonists, can improve functional recovery of the subject following a stroke. Further, the interactions between drugs and environmental factors, such as an enriched environment, can be used to improve functional recovery.

Without wishing to be bound by theory, it is believed that sigma ligands may facilitate neuronal regeneration and functional recovery by mimicking the effects of an enriched or stimulating environment.

III. Sigma Receptor Ligands

The sigma receptor ligands can be used in methods and compositions for treating neurodegenerative diseases, and for improving functional recovery from neurodegenerative diseases.

Several ligands for the sigma receptor are known which may find use with the subject methods. For example, Manallack, D. T. et al., Eur. J. Pharmacol., 144: 231-235 (1987), disclose phencyclidine compounds that have affinity for the sigma binding sites, and that the sigma site affinity was shown to be enhanced by large N-alkyl substituents, e.g., benzyl or phenylethyl. Largent, B. L. et al., Mol. Pharmacol., 32: 772-784 (1987), teach that several piperidine and piperazine derivatives have sigma receptor activity, and suggest that compounds containing more lipophilic substituents afford greater affinity for the sigma receptor binding sites. Cocaine-related compounds were shown to have sigma receptor binding activity by Sharkey, J. et al., Eur. J. Pharmacol., 149: 171-174 (1988). European Patent Application 362,001 describes α,α-disubstituted N-cycloalkylalkylamines having specific affinity for sigma receptors and European Patent Application 445,013 describes N-cycloalkylalkylamines having specific affinity for sigma receptors. The sigma receptor ligands described in both of these European applications are useful in the treatment of psychoses and gastrointestinal complaints. PCT publication WO 91/03243 includes a description of 1-cycloalkylpiperidines having specific antagonist activity toward sigma receptors and which are useful in the treatment of psychoses and dyskinesias. PCT publication WO 93/09094 includes a description of ethers derived from alkyl piperidines or pyrrolidines which are antipsychotic agents. Additional substituted piperidines and piperazines that are sigma receptor ligands are disclosed in the PCT publication WO 94/24116. The sigma receptor affinities of 1,4-(diphenylalkyl)piperazine derivatives and their use for cerebral function disorders such as dementia, depression and schizophrenia are described in U.S. Pat. Nos. 5,736,546. U.S. Pat. No. 6,087,346 discloses certain phenylalkyl-amine, aminotetralin, piperazine, piperidine and related compounds bind to the sigma receptor, and can be used for the for the treatment of central nervous system disorders, neurological disorders, gastrointestinal disorders, drug abuse, angina, migraine, hypertension and depression. Other sigma receptor ligands include BMY-14802 caramiphen and haloperidol that were found to have in vivo protective effects against NMDA-induced toxicity and seizures (M. Pontecorvo et al., (1991) Brain Res. Bull., 26:461-465). Additional sigma receptor ligands include, for example, 3PP-HCl, haloperidol, allyl-normetazocine (also called SKF 10047), normetazocine, U-50488 tartrate, carbetapentane, cyclazocine, ifenprodil, DTG(1,3-Di 2tolyl guanidine), L693,409, PTPP, 4PPBP (4-phenyl-1-(4-phenylbutyl)piperidine maleate), BD 1063, IPAB iodobenzamide, SM-21, BD1008.

IV. Methods for Identifying Sigma Receptor Ligands

Methods for identifying compounds that are sigma receptor ligands are known in the art. One method used to identify compounds that are ligands for the sigma receptor involves placing cells, tissues, or preferably a cellular extract or other preparation containing sigma receptors in contact with several known concentrations of a test compound in a buffer compatible with receptor activity, and assaying for ligand binding and/or receptor activity. The method can be performed either sequentially or in a multiplexed format. The use of in vitro binding assays with known specific ligands can allow for the determination of ligand affinities for sigma 1 or sigma 2 receptors as described in Langa F. (2003) Eur. J. Neuroscience, 18:2188-2196. Other methods for determining compounds that are ligands for the sigma receptor can be employed as will be apparent to those of skill in the art based on the disclosure herein.

The sigma ligand is preferably SA-4503 (compound IV below) or its salts, or solvates. However, all of the following compounds are sigma receptor ligands:

(I) Fluvoxamine
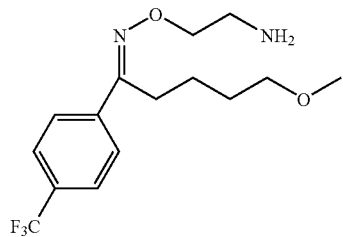

(II) 4-IBP
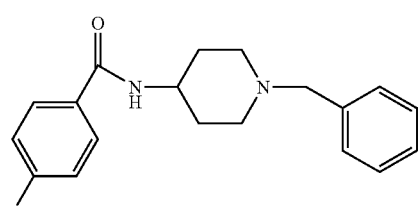

(III) PRE-084
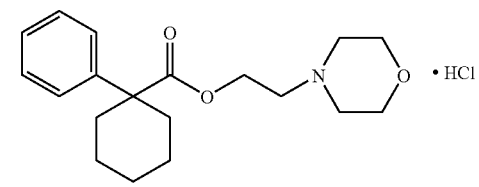

(IV) SA 4503
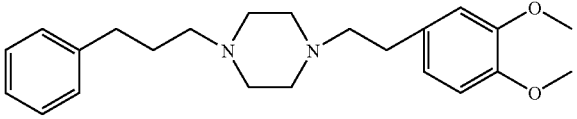

(V) Siramesine
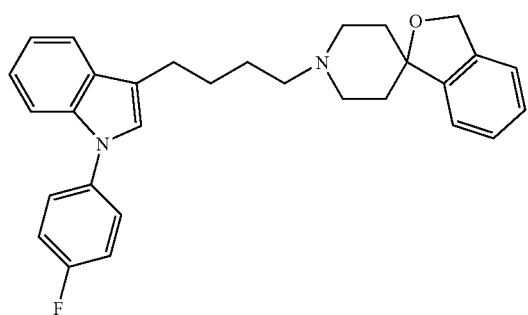

(VI) Igmesine
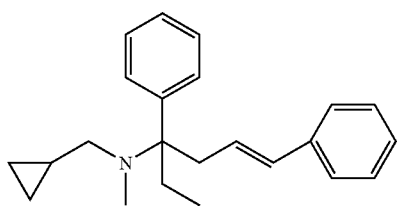

-continued (VII) OPC-14523
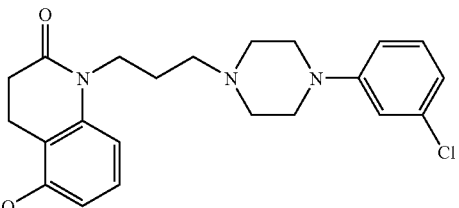

(VIII) BD-737
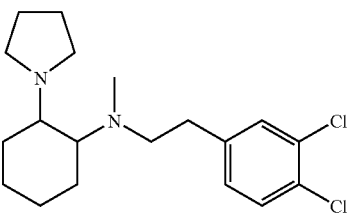

(IX) BHDP
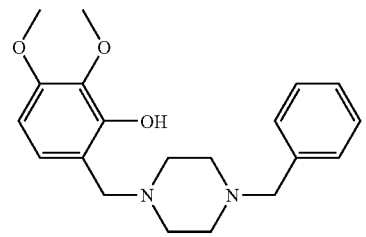

In another method, rational drug design, based upon structural studies of the molecular shapes of the sigma receptor ligands identified above and known ligands or analogs may be used to identify compounds whose three-dimensional structure is complementary to that of the active site of the sigma receptors. These compounds may be determined by a variety of techniques, including molecular mechanics calculations, molecular dynamics calculations, constrained molecular dynamics calculations in which the constraints are determined by NMR spectroscopy, distance geometry in which the distance matrix is partially determined by NMR spectroscopy, x-ray diffraction, or neutron diffraction techniques. In the case of all these techniques, the structure can be determined in the presence or absence of any ligands known to interact with sigma receptors.

The sigma receptor ligands thus identified or designed can be subsequently tested for their ability to treat and/or prevent neurodegenerative diseases. In one method, the compounds are tested for their ability to modulate the sigma receptors, such as, for example, sigma-1 (accession numbers NM_005866, NM_147157, NM_147158, NM_147159, and NM_147160), sigma-2, or recombinant sigma receptors. Lead compounds identified during these screens can serve as the basis for the synthesis of more active analogs. Lead compounds and/or active analogs generated therefrom can be formulated into pharmaceutical compositions effective in treating neurological disorders such as stroke, epilepsy and neurodegenerative disorders.

V. Synthesis of the Sigma Receptor Ligands

Some sigma receptor ligands are commercially available. Methods of preparing many are described in the patent and scientific literature, for example fluvoxamine (U.S. Pat. No. 4,085,225), 4-IBD (John et. al. (1999) Nuclear Medicine & Biology 26:377-382), Pre-084 (U.S. Pat. No. 5,223,530), SA4503 (U.S. Pat. No. 5,736,546), siramesine (U.S. Pat. No. 5,665,725), OPC-14523 (U.S. Pat. No. 5,556,857), BD-737 (U.S. Pat. No. 5,130,330 and U.S. Pat. No. 5,739,158), Igmesine (U.S. Pat. No. 5,034,419).

VI. Neuronal Regeneration and Functional Recovery

In one aspect of the invention, methods of treating a subject are provided wherein the sigma receptor ligands I-IX, or salts or solvates thereof are administered after stroke and for a sufficient period of time necessary for treatment, such as from about 1 week to about 1 month or to about 12 months or administered continuously until the desired therapeutic effect is observed. Preferably, the sigma receptor ligand is SA-4503, or salts or solvates thereof. In another aspect of the invention methods of treating a subject are provided wherein the sigma receptor ligand SA-4503, or salts or solvates thereof is administered after stroke and for a sufficient period of time necessary for treatment, such as from about 1 week to about 1 month or to about 12 months or administered continuously until the desired therapeutic effect is observed and wherein the subject is also exposed to a rich, stimulating environment, such as an enriched environment and to functional rehabilitation, so that functional recovery of the patient from the adverse consequences of the central nervous system injury is improved.

Functional recovery occurs when the functions of a damaged region of neural tissue is taken over by other areas that normally did not previously play a role in that particular function and the changes in the neural function lead to changes in behavior or in the capacity for behavior. Functional recovery is also referred to as neural plasticity. Functional recovery in the brain thus refers to functional and structural reorganization, upregulation or downregulation of a neural response to an event, and the establishment of new functional and structural connections by means of collateral sprouting and compensatory synaptogenesis as well as neurogenesis.

An improvement in the functional recovery of the patient can be assessed, for example, by using functional/behavioral tests to assess sensorimotor and reflex function of the patient's motor skills, such as posture, balance, grasp, or gait, cognitive skills, speech, and/or sensory perception and function including visual ability, taste, olfaction, and proprioception improve as a result of administrating the sigma receptor ligands according to the invention. In another aspect, functional recovery of the patient can be determined by histological analysis that includes determining the length of the axonal bundles, an increase in the neuronal regeneration at the site of injury, evaluating the dendritic morphology and the number of spines, and the like. In yet another aspect, the improvement in the functional recovery of the patient can be determined by using non-invasive techniques that determine structural alterations in the brain that lead to changes in neural function. Thus, electrophysiological (electroencephalograph (EEG) or evoked response potential (ERP)), electromyographic (EMG), neurochemical (CSF metabolites), peripheral (circulating beta-endorphin levels), radiological (CT scan, MRI) and clinical (Pupillary Light Reflex, posture, taste) measures can be used to measure functional recovery of the patients. In addition, the above techniques can be used to select patients who may be likely to successfully respond to the treatment of the invention.

The sigma receptor ligand SA-4503 is administered to mimic the effects of an enriched or stimulating environment. It is known that post-ischemic housing in an enriched or stimulating environment can improve functional outcome after brain ischemia in the rat. After an experimental brain infarction the rats housed in an enriched environment with the opportunity for various activities and interaction with other rats did better than rats housed in standard laboratory environment. An enriched environment that allowed for free physical activity combined with social interaction resulted in the best performance without change in infarct volume. An enriched environment may stimulate mechanisms that enhance brain plasticity after focal brain ischemia. It has been shown that housing rats in a stimulating environment significantly increases spine density in superficial cortical layers in intact and lesioned brain.

In one aspect of the invention, the stimulating environment comprises social interaction, motor activity, electrical stimulation of the brain, a change in the habitation, and the like. For example, the subject can be encouraged to use an impaired limb to improve sensorimotor function, may be subjected to daily physical routines, such as walking, stretching, weight lifting, and the like, or encouraged to play games, such as baseball, hockey, soccer, or board games. In addition, the domicile of the subject may be changed to stimulate brain activity, such as by changing the colors in the room, providing textured material, providing items manufactured from different materials, such as wood, steel, and the like. The knowledge to customize the stimulating environment for a particular patient is known to those in the physiotherapy and occupational therapy arts.

In another aspect, the stimulating environment comprises direct stimulation of the brain or a region of the brain. For example, electrical impulses can be applied to the brain as described in U.S. Pat. Nos. 6,339,725, and 5,611,350, and other methods known in the art. Alternatively, the brain or a region of the brain can be stimulated by localized administration of drugs, such as acetylcholine, nerve growth factors, such nerve stimulating agents, neuronal or glial growth factors and other neuronal modulating drugs.

As one of skill in the art will recognize, the timing of administering the dosage containing the sigma ligands can vary. In one aspect of the invention, the sigma receptor ligands are administered after a stroke. The administration of the ligands can be initiated within the first week of the onset of the symptoms, preferably at least 24 hours, or at least 48 hours of the onset of the symptoms. In another aspect of the invention, the sigma receptor ligands are administered to the patient concurrently with exposure to a stimulating environment. Preferably, the sigma receptor ligands are administered after a stroke at a time when the patient is subjected to a stimulating environment, and the ligands are administered for about 1 month to about 3 months to facilitate functional recovery. Preferably, the ligands, and compositions comprising the ligands are administered up to about 12 months or longer, or, even more preferably, administered continuously.

VII. Pharmaceutical Formulations and Modes of Administration

The methods described herein use pharmaceutical compositions comprising the molecules described above, where the molecule is preferably SA-4503, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, etc. Suitable excipients for non-liquid formulations are also known to those of skill in the art. Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences,* 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds of this invention will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of this invention for a given disease.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a softgel capsule or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. Typically, the compounds of the invention can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbital and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Thus, for example, capsules can be prepared by conventional procedures so that the dosage unit is 100 mg of the compounds of the invention, 100 mg of cellulose and 10 mg of magnesium stearate. A large number of unit capsules may also prepared by filling standard two-piece hard gelatin capsules each with 100 mg of powdered active ingredient, 150 mg of lactose, 50 mg of cellulose, and 10 mg magnesium stearate. Or, tablets may be prepared by conventional procedures so that the dosage unit is 100 mg of the compounds of the invention, 150 mg of lactose, 50 mg of cellulose and 10 mg of magnesium stearate. A large number of tablets may also be prepared by conventional procedures such that the dosage unit was 100 mg of the compounds of the invention, and other ingredients can be 0.2 mg of colloidal silicon dioxide, 5 mg of magnesium stearate, 250 mg of microcrystalline cellulose, 10 mg of starch and 100 mg of lactose. Appropriate coatings may be applied to increase palatability or delay absorption.

When liquid suspensions are used, the active agent may be combined with any oral, non-toxic, pharmaceutically acceptable inert carrier such as ethanol, glycerol, water, and the like and with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the present invention into the body of a patient through a needle or a catheter, propelled by a sterile syringe or some other mechanical device such as an continuous infusion system. A formulation provided by the present invention can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

The formulations can optionally contain an isotonicity agent. The formulations preferably contain an isotonicity agent, and glycerin is the most preferred isotonicity agent. The concentration of glycerin, when it is used, is in the range known in the art, such as, for example, about 1 mg/mL to about 20 mg/mL.

The pH of the parenteral formulations can be controlled by a buffering agent, such as phosphare, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and may be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions are prepared by incorporating one or more of the compounds of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the invention may be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the invention may also be delivered through the skin or muscosal tissue using conventional transdermal drug delivery systems, i.e., transdernal "patches" wherein the agent is typically contained within a laminated structure that serves as a drug delivery device to be affixed to the body surface. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present invention, generally a therapeutic amount will be in the range of about 0.01 mg/kg to about 40 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject may be administered as many doses as is required to reduce and/or alleviate the signs, symptoms, or causes of the disorder in question, or bring about any other desired alteration of a biological system.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

VIII. Kits

In another aspect, the invention relates to pharmaceutical compositions in kit form. The kit comprises container means for containing the compositions such as a bottle, a foil packet, or another type of container. Typically the kit further comprises directions for the administration of the compositions.

In another aspect, a packaged kit is provided that contains the pharmaceutical formulation to be administered, i.e., a pharmaceutical formulation containing a ligand for the sigma receptor for the treatment of a neurodegenerative disease to facilitate neuronal regeneration or functional recovery, a container, preferably sealed, for housing the formulation during storage and prior to use, and instructions for carrying out drug administration in a manner effective to treat the disease. The instructions will typically be written instructions on a package insert and/or on a label. The formulation may be any suitable formulation as described herein. For example, the formulation may be an oral dosage form containing a unit dosage of the ligand for the sigma receptor. The kit may contain multiple formulations of different dosages of the same agent. The kit may also contain multiple formulations of different active agents.

For example, the kits for parenteral administration can comprise a) a pharmaceutical composition comprising SA-4503 described above and a pharmaceutically acceptable carrier, vehicle or diluent; and, optionally, b) instructions describing a method of using the pharmaceutical composition for treating or preventing the disease. The kits can further include a device for administering the formulation (e.g., a syringe, a catheter, and the like). The kits for oral administration can comprise the dosage formulation contained within a container, such as, for example, a paper or cardboard box, a glass or plastic bottle or jar, a re-sealable bag, or a blister pack with individual doses. Blister packs generally consist of a sheet of relatively stiff material covered with a foil of a preferably transparent plastic material. During the packaging process, having recesses the size and shape of the tablets or capsules, are formed in the plastic foil. Subsequently, the tablets or capsules are placed in the recesses and the sheet of relatively stiff material is sealed against the plastic foil at the face of the foil which is opposite from the direction in which the recesses were formed. As a result, the tablets or capsules are individually sealed. Preferably the strength of the sheet is such that the tablets or capsules can be removed from the blister pack by manually applying pressure on the recesses whereby an opening is formed in the sheet at the place of the recess. The tablet or capsule can then be removed via the opening.

It may be desirable to provide a memory aid on the kit, e.g., in the form of numbers next to the, tablets or capsules whereby the numbers correspond with the days of the regimen which the dosage form so specified should be administered. Another example of such a memory aid is a calendar printed on the card e.g., as follows "First Week, Monday, Tuesday, . . . etc. . . . Second Week, Monday, Tuesday, . . . " etc. Other variations of memory aids will be readily apparent, such as, for example, a mechanical counter which indicates the number of daily doses that has been dispensed, a microchip memory coupled with a liquid crystal readout, or audible reminder signal which, for example, reads out the date that the last daily dose has been taken and/or reminds one when the next dose is to be taken, and the like.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Animal Models for Neuronal Regeneration (Functional Recovery)

Male 3 months old SHR (spontaneous hypertensive) rats are used for induction of stroke by MCA occlusion. This is the preferred strain since most stroke patients are hypertensive. The animals are anesthetized with Methohexital and a small craniectomy is made above the zygmotic arch to expose the middle cerebral artery, which is occluded with a 10-0 monofilament nylon thread distal to the origin of the striatal branches. The rats are not intubated and no catheters are inserted. Following MCA occlusion a large and reproducible infarct is obtained, leading to a robust sensorimotor deficit. The animals are kept on a 6 hr light/18 h dark cycle with free access to food and water. At two days after the MCAO the rats are treated with the compound I, II, III, IV, V, VI, VII, VIII, or IX (0.03-10 mg/kg) s.c. or p.o. and a control group is given saline for 2-8 weeks. At 2, 4, 6 and 8 weeks animals are tested in the rotating pole or cylinder test Rotating pole: This test allows for the rapid assessment of coordination and integration of motor movement, by the ability of the rat to traverse a rotating pole as described previously (Johansson and Ohlsson, (1995) Stroke 26: 644-649. The pole has a length of 1500 mm, is elevated 750 mm above the floor and rotates at 10 rpm to the right or left, respectively.

A score of 6-0 is given for each direction:

6, the animal crosses the pole with no foot slips;
5, the animal crosses the pole with a few foot slips;
4, the animal crosses the pole, slipping 50% of the footsteps;
3, the animal crosses the pole with more than 50% foot slips;
2, the animal walks a bit and then rotates around the pole;
1, the animal rotates around the pole without crossing it;
0, the animal falls off the pole.

Cylinder Test for Asymmetric Use of Forelimb Use in Spontaneous Rearing

The cylinder test (modified from Schallert and Tillerson (Innovative models of CNS disease: from molecule to therapy. Clifton, N.J., Humana, 1999) is used to quantify the forelimb use for rearing on the cylinder wall. The rats are monitored as they move freely in a 20-cm-wide clear glass cylinder. Contacts made by each forepaw with the cylinder wall while rearing are scored by a blinded observer. A total of 20 contacts are recorded for each animal, and the number of impaired (left), both, and non-impaired forelimb contacts as percentage of total contacts is calculated. Baseline for rats is achieved by measuring the contacts made by each forepaw before MCAO.

When using the rotating pole test or the cylinder test, the group of animals that are given compounds I, II, III, IV, V, VI, VII, VIII, or IX perform better than the group 1 control animals. Thus, animals suffering from central nervous system disorders show enhanced functional recovery when administered sigma receptor ligands.

Example 2

Evidence of Neuronal Regeneration in Rats Treated with SA4503

1. Rotating Pole

Thirty five spontaneously hypertensive rats were exposed to permanent middle artery occlusion (MCAO), then divided into three treatment groups. Starting at two days after occlusion and continuing daily until 28 days after occlusion, SA4503 was administered s.c. in doses of 0.3 mg/kg (12 rats) or 1.0 mg/kg (12 rats). In a control group (11 rats), vehicle only was administered. At the start of treatment, and at several time points during the test, the rats were assessed for their performance in the rotating pole model. This model is described in Example 1. It requires the rats to cross a horizontally suspended rotating pole having a length of 1 m. This task measures the sensory-motor performance of the animals. The animals' behaviour was recorded using a video camera and later analyzed and scored by a trained technician. The scoring ranges from 0 to 6, with 0 being very poor performance and 6 reflecting the performance of a healthy animal (without MCAO). The results are given in Table 1.

TABLE 1

| DOSE | Average Increase in Score at Day 30 (SEM) |
|---|---|
| Vehicle | 1.8 (SEM 0.5) (p < 0.05) |
| 0.3 mg/kg | 3.5 (SEM 0.4) (p < 0.05) |
| 1.0 mg/kg | 3.67 (SEM 0.48) (p < 0.05) |

The group treated with 0.3 mg/kg SA4503 demonstrated a total average score of 5.2 at day 30, which is close to that expected of healthy animals.

Thus, this test demonstrates that the sigma-1 selective agonist, SA4503 facilitates functional recovery, in particular recovery in a motor skill, when administered daily to rats in a model of ischemic stroke from 2 days after the stroke until 28 days after the stroke for 28 days.

2. Cylinder Test

Forty three spontaneously hypertensive rats were exposed to permanent middle artery occlusion (MCAO), then divided into three treatment groups. Starting at two days after occlusion and continuing daily for 14 days, SA4503 was administered p.o. in doses of 0.1 mg/kg (14 rats) or 0.3 mg/kg (14 rats). In a control group (15 rats), vehicle only was administered. At the start of treatment, and at several time points during the test, the rats were assessed for their performance in the cylinder test. This test is described in Example 1. It measures the sensory-motor performance of the animals. The performance of the rats in the test was assessed one day before permanent MCAO, then at 14 days, 28 days and 59 days after permanent MCAO. The rats were monitored as they moved freely in a 20 cm-wide clear glass cylinder. Contacts made by each forepaw with the cylinder wall while rearing were scored by a blinded observer. A total of 20 contacts were recorded for each animal, and the number of impaired (left), both, and non-impaired forelimb contacts as a percentage of total contacts was calculated. The results are given in Table 2.

TAABLE 2

PAW USAGE (% DIFFERENCE IN NUMBER OF CONTACTS MADE WITH LEFT AND RIGHT PAW)

| DOSE | Pre-MCAO (SEM) | Day 14 (SEM) | Day 28 (SEM) | Day 59 (SEM) |
|---|---|---|---|---|
| VEHICLE | 3.86 (4.9) | 35.6 (8.9) | 30.3 (8.4) | 40.1 (11) |
| 0.1 mg/kg | −2.78 (6.5) | 25.79 (11.4) | 11.14 (8) | 32.64 (12.5) |
| 0.3 mg/kg | 8.2 (5.7) | 7.79 (8.18) | 6.28 (7.96) | 6.28 (8.81) |

Asymmetry of paw usage (% difference left/right) is a consequence of permanent MCAO. Animals pre-MCAO did not show any asymmetric behaviour. Vehicle treated animals remained asymmetric throughout the observation period. Animals treated with 0.3 mg/kg SA4503 had their asymmetry of paw usage reduced to pre-MCAO levels at all time points measured.

Thus, this test demonstrates that the sigma-1 selective agonist, SA4503 facilitates functional recovery, in particular recovery in a motor skill, when administered daily to rats in a model of ischemic stroke from 2 days after the stroke for 14 days.

Example 3

Gene Expression Studies

The Ethics Committee for Animal Research at Lund University approved the experimental protocol. Six-month-old male SHR (spontaneous hypertensive rats), obtained from Mollegard Breeding Center, Ejby, Denmark, 2 months earlier and preoperatively housed in standard cages (550×350×200 mm, 3 to 4 rats in each cage), were anesthetized with methohexital sodium (Brietal, 37° C.) 50 mg/kg intraperitoneally. The right MCA was accessed via a small craniotomy, and the artery was ligated distal to the striatal arteries, causing a neocortical infarct. The mean surgery time was about 20 minutes and body temperature was maintained close to 37° C. Postoperatively, rats were kept in individual cages for 24 hours. The rats subjected to MCA occlusion (MCAO) were either returned to standard environment (SE), or were placed in a large, vertical, enriched-environment (EE) cage (815× 610×1,280 mm), equipped with horizontal and vertical boards, chains, swings, wooden blocks, and objects of different sizes and materials. The distance between the boards and the movable objects was changed twice a week. The sham group were subjected to a sham surgery without MCAO and placed in the standard environment. In all experimental groups 12 and 60 days of recovery were selected as end point analysis of gene expression. The study was conducted using 6 experimental groups, with each group composed of 6-8 animals.

The animals were sacrificed after 12 and 60 days from each experimental group and tissues from the medial, rostral and frontal cortex as well as hippocampus and striatum regions of the brain were isolated for RNA purification and target preparation. cDNA arrays consisting of 50,000 clones from a rat cortex cDNA library were hybridized with labeled target nucleic acid obtained from control, standard MCAO and enriched environment animals. About 3400 upregulated genes were selected after bioinformatics analysis of the resulting gene discovery array data. The raw clone data was normalized by the median empty well value for each respective array filter. These values were then transformed (log2+1) to approximate normality. All replicates where then pooled for subsequent statistical analysis. For each brain region (frontal, medial, rostral, hippocampus and striatum) the time points of the three experimental conditions (enriched environment, stroke and control) where analyzed by principal component analysis (PCA). The outlying data points where removed from the data set. Next an ANOVA was performed with regard to a clone's behavior among the experimental conditions within a given brain region and time point. The results of the ANOVA were filtered for clones that had a p-value less than 0.05. This filtered ANOVA list was then analyzed with the Tukey HSD test to determine the clone's expression pattern.

Selection was based on expression upregulation of $\geq 1.8$-fold and a coefficient of variation (cv) of <0.2. The selected clones were picked, amplified by PCR, and re-printed on nylon membranes for profiling arrays. The profiling arrays were probed with probes from different cortical and subcortical regions and recovery times of 12 and 60 days. Clones that were upregulated were selected for further analysis.

Analysis of the data from discovery and profiling arrays allowed for the identification of potential mechanistic pathways in the pathophysiology of ischemic stroke and intracellular mechanism of functional recovery after enriched-environment. This analysis included principal component analysis of regulated clones, as well as clustering of regulated genes with similar expression profiles. Principal component analysis yields a causality relationship among sets of genes clusters. Selection of regulated genes as potential intervention targets for Central Nervous System (CNS) disorders included, a series of criteria including, but not limited to, sequence annotation, expression profile, placement of the gene within mechanistic pathways of biological relevance in the pathology of CNS disorders, technical feasibility to develop drugs directed to modulate the specific gene (i.e. drugability), known biological role of a gene in CNS or other organ pathologies.

Analysis of EE array data demonstrated that in striatum and frontal cortex, type 1 sigma receptor mRNA is upregulated while in medial cortex, type 1 sigma receptor mRNA is downregulated when the animals were placed in an enriched compared to standard environment. Thus, stimulation of brain by application of an enriched environment induces expression of the type 1 sigma receptor in brain regions important for control of sensory-motor functions.

Example 4

Preparation of Tablets

The compound of formula IV (10.0 g) is mixed with lactose (85.5 g), hydroxypropyl cellulose HPC-SL (2.0 g), hydroxypropyl cellulose L-HPC, LH-22 (2.0 g) and purified water (9.0 g), the resulting mixture is subjected to granulation, drying and grading, and the thus obtained granules are mixed with magnesium stearate (0.5 g) and subjected to tablet making, thereby obtaining tablets containing 10 mg per tablet of the compound of formula IV.

Example 5

Administering to a Subject

The tablet prepared in Example 4 is provided to a subject at time 0. One tablet every 24 h is provided for a period of one week. After administration of the third tablet, the subject is exposed to a neurodegenerative event. The treated subject exhibits symptoms of neurological disorder that are less severe compared to the subject that was not treated.

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

The invention claimed is:

1. A method of treating a neurodegenerative disease selected from the group consisting of stroke, spinal cord injury, and traumatic brain injury, comprising administering to a mammalian subject a therapeutically effective amount of 1-(3,4-dimethoxyphenethyl)-4-(3-phenylpropyl) piperazine, or a pharmaceutically acceptable salt thereof, more than twenty-four hours after onset of said neurodegenerative disease to facilitate functional recovery.

2. The method of claim 1, wherein administration is initiated more than twenty-four hours and within forty-eight hours following onset of symptoms of the neurodegenerative disease.

3. The method of claim 1, wherein administration is initiated more than forty-eight hours and within the first week following onset of symptoms of the neurodegenerative disease.

4. A method of treating a mammalian subject after onset of a neurodegenerative disease selected from the group consisting of stroke, spinal cord injury, and traumatic brain injury, comprising administering to the subject a therapeutically effective amount of 1-(3,4-dimethoxyphenethyl)-4-(3-phenylpropyl) piperazine, or a pharmaceutically acceptable salt thereof, more than twenty-four hours after onset of said neurodegenerative disease, and continuing administration thereafter.

5. The method of claim 4, wherein administration is continued for one to three months.

6. The method of claim 4, wherein administration is continued daily.

7. The method of claim 4, wherein the subject is a human.

8. A method of treating stroke, comprising administering to a patient suffering from stroke a therapeutically effective amount of 1-(3,4-dimethoxyphenethyl)-4-(3-phenylpropyl) piperazine, or a pharmaceutically acceptable salt thereof, more than twenty-four hours after onset of symptoms of stroke, and continuing administration thereafter.

9. The method of claim 8, wherein administration is continued for one to three months.

10. The method of claim 8, wherein administration is continued daily.

11. The method of claim 1, wherein the salt is the hydrochloride salt or the dihydrochloride salt.

12. The method of claim 1, wherein the pharmaceutically acceptable amount is delivered to the patient in the range of about 1 mg to about 300 mg per dose.

13. The method of claim 1, wherein the subject is a human.

14. The method of claim 4, wherein the salt is the hydrochloride salt or the dihydrochloride salt.

15. The method of claim 4, wherein the pharmaceutically acceptable amount is delivered to the patient in the range of about 1 mg to 300 mg per dose.

16. The method of claim 4, wherein the pharmaceutically acceptable amount is delivered to the patient in the range of about 1 mg to 6 mg per dose.

17. The method of claim 8 wherein the salt is the hydrochloride salt or the dihydrochloride salt.

18. The method of claim 8, wherein the stroke is ischemic stroke.

19. The method of claim 18, wherein the ischemia is focal ischemia or global ischemia.

20. The method of claim 8, wherein the pharmaceutically acceptable amount is delivered to the patient in the range of about 1 mg to 300 mg per dose.

21. The method of claim 8, wherein the pharmaceutically acceptable amount is delivered to the patient in the range of about 1 mg to 6 mg per dose.

22. The method of claim 8, wherein administration is initiated more than twenty-four hours and within forty-eight hours after onset.

* * * * *